US009274278B2

United States Patent
Okayama

(10) Patent No.: US 9,274,278 B2
(45) Date of Patent: Mar. 1, 2016

(54) OPTICAL WAVEGUIDE ELEMENT

(71) Applicant: Oki Electric Industry Co., Ltd., Tokyo (JP)

(72) Inventor: Hideaki Okayama, Tokyo (JP)

(73) Assignee: OKI ELECTRIC INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 14/743,380

(22) Filed: Jun. 18, 2015

(65) Prior Publication Data

US 2016/0011370 A1     Jan. 14, 2016

(30) Foreign Application Priority Data

Jul. 14, 2014    (JP) .................................. 2014-144261

(51) Int. Cl.
    *G02B 6/10*        (2006.01)
    *G02B 6/12*        (2006.01)
    *G02B 6/28*        (2006.01)
            (Continued)

(52) U.S. Cl.
    CPC ............ *G02B 6/125* (2013.01); *G02B 6/12007* (2013.01); *G02B 6/1228* (2013.01); *G02B 6/29344* (2013.01); *G01N 21/3504* (2013.01); *G02B 6/1225* (2013.01); *G02B 6/26* (2013.01);
            (Continued)

(58) Field of Classification Search
    CPC .... G02B 6/1225; G02B 6/1228; G02B 6/125; G01N 21/3504
    USPC ........ 385/14, 16, 31–37, 131, 12; 372/43–50, 372/102; 428/82.11
    See application file for complete search history.

(56) References Cited

U.S. PATENT DOCUMENTS 5,189,714 A    *    2/1993    Okayama .............. G02F 1/3133
                                                        385/27
5,689,597 A        11/1997    Besse
                    (Continued)

FOREIGN PATENT DOCUMENTS

JP        H08-508351 A     9/1996
JP        2004-325999 A    11/2004
           (Continued)

OTHER PUBLICATIONS

Emil Kleijn et al., "Multimode Interference Couplers With Reduced Parasitic Reflections", IEEE Photonics Technology Letters, vol. 26, No. 4, pp. 408-410, Feb. 15, 2014.

*Primary Examiner* — Akm Enayet Ullah
(74) *Attorney, Agent, or Firm* — Rabin & Berdo, P.C.

(57) ABSTRACT

An optical waveguide element includes a waveguide core formed of silicon, and a cladding layer formed of a material identical to the waveguide core for enveloping the waveguide core. The optical waveguide element comprising: a high-order propagation mode waveguide; a single input tapered waveguide that is provided on an input terminal of the high-order propagation mode waveguide; a plurality of output tapered waveguides that are provided on an output terminal of the high-order propagation mode waveguide; and an optical feedback elimination waveguide that is provided on the input terminal and disposed alongside the input tapered waveguide. In the optical waveguide element, the input tapered waveguide and the output tapered waveguides are tapered waveguides in which a waveguide width becomes gradually narrower the greater the separation from a terminal of connection to the high-order propagation mode waveguide, and the optical feedback elimination waveguide eliminates reflected light into the cladding layer.

10 Claims, 5 Drawing Sheets

(51) Int. Cl.
  *G02B 6/42* (2006.01)
  *G02B 6/125* (2006.01)
  *G02B 6/293* (2006.01)
  *G02B 6/122* (2006.01)
  *G02B 6/26* (2006.01)
  *G01N 21/3504* (2014.01)

(52) U.S. Cl.
  CPC ............ *G02B 2006/12109* (2013.01); *G02B 2006/12147* (2013.01)

(56) References Cited

U.S. PATENT DOCUMENTS

| | | | |
|---|---|---|---|
| 6,470,112 B2* | 10/2002 | Okayama | H04B 10/801 385/24 |
| 6,728,435 B2* | 4/2004 | Kashihara | G02B 6/12016 385/20 |
| 7,313,297 B2* | 12/2007 | Yanagisawa | G02B 6/12007 385/14 |
| 8,538,208 B2* | 9/2013 | Ho | G02B 6/0281 385/131 |
| 9,151,898 B2* | 10/2015 | Okayama | G02B 6/30 |
| 2004/0228579 A1 | 11/2004 | Kondo | |
| 2013/0259425 A1 | 10/2013 | Okayama | |

FOREIGN PATENT DOCUMENTS

| | | |
|---|---|---|
| JP | 2010-079317 A | 4/2010 |
| JP | 2013-210503 A | 10/2013 |

* cited by examiner

OPTICAL WAVEGUIDE ELEMENT

CROSS REFERENCE TO RELATED APPLICATION(S)

This application is based upon and claims benefit of priority from Japanese Patent Application No. 2014-144261, filed on Jul. 14, 2014, the entire contents of which are incorporated herein by reference.

BACKGROUND

The present invention relates to an optical waveguide element that functions as a branching element or a wavelength filter.

In recent years, an optical waveguide element that has a waveguide core made of silicon is attracting attention. An optical waveguide that is formed by enclosing a silicon waveguide core in a cladding layer of a material having a lower refractive index than silicon (silicon oxide or silicon nitride, for example) is referred to as a silicon waveguide. The silicon waveguide achieves an extremely high difference in the refractive indices between the core and the cladding layer and thus, if a silicon waveguide is used, a compact optical waveguide element can be realized.

Further, if the optical waveguide element using silicon as the waveguide core uses a silicon on insulator (SOI) substrate, it is possible to form the optical waveguide element using known etching processing, chemical vapor deposition (CVD) etc., which are used in the manufacturing processes of integrated circuits and optical waveguide elements and the like. As a result, there is the advantage that it is not necessary to develop new manufacturing processes. Further, a characteristic of these manufacturing processes is that they are suitable for mass production.

A branching element and a wavelength filter are essential elements when constructing an optical communication system or the like, and known optical waveguide type branching elements include an element that uses a Y-branch waveguide, an element that uses a directional coupler and an element that uses multimode interference (MMI) (refer to JP-T-8-508351 and to E. Kleijn, et al., "Multimode Interference Couplers With Reduced Parasitic Reflections" IEEE Photonics Technology Letters, Vol. 26, pp. 408-410 (2014).)

SUMMARY

In an optical waveguide type branching element or a wavelength filter, in general, some of input light is reflected back from an output side and returns to the input side, and is once more reflected back to an output terminal, and becomes noise with respect to an output signal light. There is a problem that it is not possible to ignore an amount of this light (hereinafter sometimes referred to as optical noise).

Even in an optical waveguide element that is made of a compound semiconductor, or an optical waveguide element that is made of a silicon material, in an element with a rib configuration, this optical noise is not large enough to cause a problem in use, but in a silicon waveguide or an MMI type optical waveguide element that has a silicon core, when a difference in the refractive index between the core and the cladding layer is large, there are cases in which the amount of optical noise is of a magnitude that cannot be ignored in practical use.

Here, an inventor of the present invention examined a reduction in the amount of optical noise, in an MMI type optical waveguide element that has silicon as the waveguide core. As a result of the examination, it was revealed that if a structure is provided in which optical feedback that is reflected back to an input terminal side of a higher-order mode waveguide that configures the optical waveguide element (hereinafter also referred to as and MMI waveguide) is efficiently led from the silicon core to the cladding layer and eliminated, with respect to optical feedback, it is possible to reduce the amount of light that is once more reflected and reaches an output terminal, and that becomes mixed with an output signal.

In other words, there has been a demand to provide an optical waveguide element in which an amount of optical noise that is mixed with output light is reduced.

According to the one embodiment of the present invention, an optical waveguide element may comprise the following.

The optical waveguide element according to the one embodiment of the present invention has a waveguide core formed of silicon, and a cladding layer formed of a material identical to the waveguide core for enveloping the waveguide core. The optical waveguide element comprises: a single input tapered waveguide that is provided on an input terminal of MMI waveguide; and a plurality of output tapered waveguides that are provided on an output terminal of the MMI waveguide. The input tapered waveguide is disposed side by side with the input terminal and an optical feedback elimination waveguide is provided, which eliminates, into the cladding layer, reflected (feedback) light that is input from the input terminal and reflected by the output terminal. The input tapered waveguide and the output tapered waveguides are tapered waveguides in which a waveguide width becomes gradually narrower the further the waveguide is distanced from an end that is bonded to the MMI waveguide.

A waveguide width of MMI waveguide is set according to a number of the output tapered waveguides. In case that a number N of the output tapered waveguides is provided (N is an integer of 2 or more), it is preferable that a waveguide width of the MMI waveguide is set to be capable of propagating at least N types of a propagation mode.

Without being limited to one optical feedback elimination waveguide, the optical feedback elimination waveguides may be provided on both sides of and sandwich the input tapered waveguide.

It is preferable that the optical feedback elimination waveguide has a guided light reflection waveguide side surface, to reflect the light guided to the optical feedback elimination waveguide (the feedback light reflected back to the input terminal side of the MMI waveguide) in a direction displaced from a direction of direct reflection with respect to the guiding direction of the MMI waveguide. Also, it is preferable that the optical feedback elimination waveguide comprises a reflection suppression structure. As described below, the reflection suppression structure efficiently leads the feedback light guided to the optical feedback elimination waveguide or and absorb etc.

The optical waveguide element of the present invention is provided with an optical feedback elimination waveguide and thus the optical waveguide element guides optical feedback, which is a part of input light that is reflected from an output side and that returns to an input side, to the optical feedback elimination waveguide. Specifically, the optical feedback elimination waveguide is adopted as a structure to efficiently guide the optical feedback from the silicon core to the cladding layer and thus eliminate the optical feedback.

As a result, an effect is obtained by which an amount of light that is once more reflected from the input side and reaches the output side is reduced and optical noise is accordingly reduced. In particular, if the optical feedback elimination waveguide is structured to have a guided light reflection waveguide side surface, an amount of light guided to the optical feedback elimination waveguide is increased and the optical feedback is more effectively eliminated. Further, by also providing the optical feedback elimination waveguide with a reflection suppression structure, it is possible to even more effectively eliminate the optical feedback.

DETAILED DESCRIPTION OF THE EMBODIMENT(S)

Figure 1A:
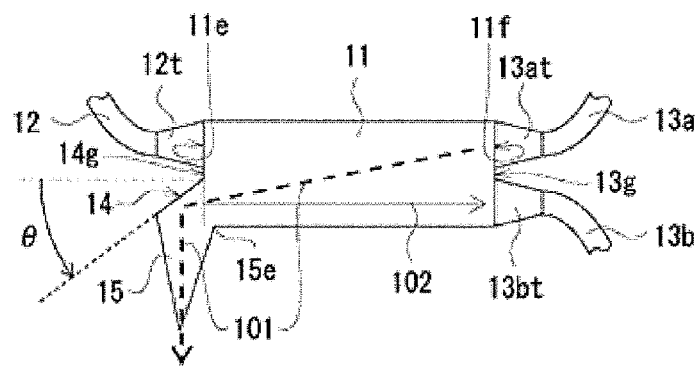
FIG. 1A is a basic schematic diagram contributing to an explanation of a principle of operation of a waveguide pattern of an optical waveguide element according to an embodiment of the present invention.

Hereinafter, referring to the appended drawings, preferred embodiments of the present invention will be described in detail. It should be noted that, in this specification and the appended drawings, structural elements that have substantially the same function and structure are denoted with the same reference numerals, and repeated explanation thereof is omitted.

<Optical Waveguide Element>

Figure 1B:
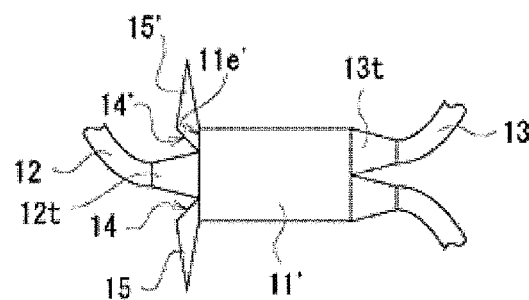
FIG. 1B shows a configuration example in which, in the waveguide pattern of the optical waveguide element according to the embodiment of the present embodiment, optical feedback elimination waveguides are provided on both sides of an input tapered waveguide and sandwich the input tapered waveguide.
Figure 1C:
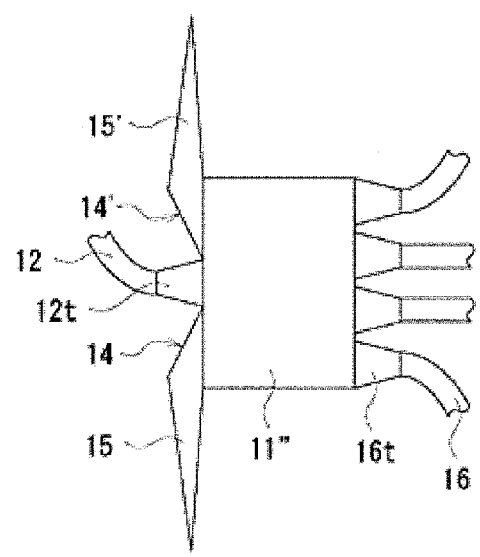
FIG. 1C shows a configuration example in which, in the waveguide pattern of the optical waveguide element according to the embodiment of the present embodiment, four output tapered waveguides are provided.
Figure 1D:
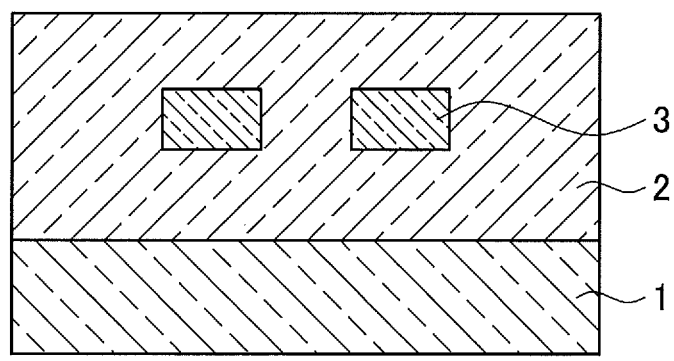
FIG. 1D is an overall schematic view showing a vertical cross-section of a waveguide of the optical waveguide element according to the embodiment of the present embodiment.

A basic configuration of an optical waveguide element according to an embodiment of the present invention will be explained with reference to FIG. 1A. FIG. 1A to FIG. 1C show a shape of a silicon core as seen from a direction vertical to a substrate surface of the optical waveguide element, namely, show a waveguide pattern. FIG. 1D shows a vertical cross-section of a waveguide of the optical waveguide element according to the embodiment of the present invention.

The optical waveguide element shown in FIG. 1A is provided with a single input tapered waveguide 12*t* on an input terminal 11*e* of an MMI waveguide 11 and is provided with two output tapered waveguides 13*at* and 13*bt* on an output terminal 11*f*. The input tapered waveguide 12*t* and the output tapered waveguides 13*at* and 13*bt* are tapered waveguides in which a waveguide width becomes gradually narrower the further the waveguide is distanced from an end that is bonded to the MMI waveguide 11. The input tapered waveguide 12*t* is disposed side by side with the input terminal 11*e* and an optical feedback elimination waveguide 15 is provided, which eliminates reflected light propagated through the MMI waveguide 11 in a direction opposite to a direction of propagation of input light input from the input terminal 11*e*.

The optical waveguide element shown in FIG. 1A is a one-input two-output type splitter element, but it can be used as a wavelength filter, by adjusting a length in a guiding direction of the MMI waveguide 11. This optical waveguide element is provided with the two output tapered waveguides and thus the MMI waveguide 11 is set to a waveguide width in which two or more propagation modes can be excited. In general, the waveguide width of the MMI waveguide 11 that forms the same type of the optical waveguide element provided with N number of output tapered waveguides is set to a waveguide width in which N types of propagation modes can be excited.

The optical waveguide element shown in FIG. 1A is not only able to be used as the branching element, as described above, but can also be used as a multiplexer that is provided with a function as a wavelength filter that is suitable to be provided in a subscriber terminal in an optical communication system. Namely, the optical waveguide element can be installed in a device on the side of the subscriber in the optical communication system and can be caused to function as a waveguide switching element for a downstream signal from a station side to the subscriber side and an upstream signal from the subscriber side to the station side. In this case, for example, the downstream signal is input from the input tapered waveguide 12*t* and is output from the output tapered waveguide 13*bt*. Meanwhile, the upstream signal is input from a port designated as the output tapered waveguide 13*bt* and is output from the input tapered waveguide 12*t*.

Here, for ease of explanation, the input tapered waveguide and the output tapered waveguide are named, but depending on a usage mode, input may be performed on a waveguide that is designated for output or output may be performed from a waveguide that is designated for input, and the input terminal and output terminal are not limited to that.

A fundamental propagation mode waveguide 12 is connected to the input side input tapered waveguide 12*t*, and fundamental propagation mode waveguides 13*a* and 13*b* are respectively connected to the two output side output tapered waveguides 13*at* and 13*bt*. If the optical waveguide element is provided with the input waveguide and the two output waveguides, the functions as the branching element or the wavelength filter are realized, but in many usage examples of the optical waveguide element, the input light and the output light are in the fundamental propagation mode. Therefore, the input tapered waveguide 12*t* and the two output tapered waveguides 13*at* and 13*bt* function as connecting waveguides in order to connect the fundamental propagation mode waveguides 12, 13a and 13b to the optical waveguide element with low light loss.

A gap 13g is provided between the two output tapered waveguides 13at and 13bt. Due to the provision of the gap 13g, a part of the component of the light reaching this section is reflected, and the remaining component penetrates (leaks) into the cladding layer and is lost. In order to reduce the reflected light and the optical electric field component of the leaked light as much as possible, it is necessary to make the gap 13g as narrow as possible. For example, when assuming a wavelength bandwidth used in optical communication of 1 pm as the guided light, it is preferable for the gap 13g to be set as 300 nm or less.

The gap 13g is formed in consideration of technological reasons arising from the lithography process or the etching process in forming the element. Specifically, the gap 13g is formed in consideration of resolution limits in the lithography process and limits in formation accuracy due to the way the etching gas flows in the etching process.

A lower limit of the gap 13g is approximately 200 nm, taking into consideration a formation accuracy etc. in the dry etching process used in the forming process of the optical waveguide element.

The component of light reflected from an output side end surface (the gap 13g) of the MMI waveguide 11 is propagated through a path 101 (shown by a thick broken line) toward an input terminal 11e, and if the optical feedback elimination waveguide 15 is not provided, the light component is reflected again by the input terminal 11e on the side of the input tapered waveguide 12t of the MMI waveguide 11, is propagated through a path 102 and is mixed with the output tapered waveguide 13bt.

In a known optical waveguide element of a same type as the optical waveguide element shown in FIG. 1A, the optical feedback elimination waveguide 15 is not provided and a shape is obtained in which the silicon core is not provided further to the outside than the end surface on the input side (shown as the an input terminal 11e in FIG. 1A) of the MMI waveguide 11. In the known optical waveguide element, as the optical feedback elimination waveguide 15 is not provided, the light component is reflected from the output terminal 11f of the MMI waveguide 11 and is reflected by the input terminal 11e, is then propagated through the path 102 and is input to the output tapered waveguide 13bt. As a result, it is impossible to ignore an effect of interference with a communication optical signal from the input tapered waveguide 12t toward the output tapered waveguide 13bt.

In contrast to this, in the optical waveguide element according to the embodiment of the present invention, the optical feedback elimination waveguide 15 that eliminates the reflected light propagated through the MMI waveguide 11 is provided, and the optical feedback elimination waveguide 15 has a guided light reflection waveguide side surface 14 to reflect the light guided to the optical feedback elimination waveguide 15 in a direction displaced from a direction of direct reflection with respect to the guiding direction of the MMI waveguide 11.

With the optical waveguide element according to the embodiment of the present invention, the reflected light that is propagated through the path 102 and propagated toward the output tapered waveguide 13bt is reflected by the guided light reflection waveguide side surface 14 and is guided to the optical feedback elimination waveguide 15.

In the optical waveguide element shown in FIG. 1A, as a reflection suppression structure, the optical feedback elimination waveguide 15 adopts the tapered structure and a leading end of the waveguide has a waveguide width of several tens nm. As a result, an amount of reflected light at the leading end of the optical feedback elimination waveguide 15 is equal to or less than −30 dB. Therefore, the guided light that may be reflected by the input terminal 11e of the MMI waveguide 11 and mixed with the output tapered waveguide 13bt is eliminated into the cladding layer from the optical feedback elimination waveguide 15 and does not influence the communication signal light output from the output tapered waveguide 13bt.

It is preferable that a gap 14g between the guided light reflection waveguide side surface 14, which is a part of the optical feedback elimination waveguide 15, and a side surface of the input tapered waveguide 12t also be as narrow as possible. This is because a component of the light that is reflected by the gap 14g is mixed with the output tapered waveguides 13at and 13bt. In order to make the gap 14g narrow, it is effective if a direction of the guided light reflection waveguide side surface 14 is caused to be tilted at an angle θ that is as large as possible with respect to the guiding direction of the MMI waveguide 11.

It is preferable that an intersection point 15e between one side surface of the optical feedback elimination waveguide 15 and a side surface of the MMI waveguide 11 be set such that it is in a position further to the side of the MMI waveguide 11 than the input terminal 11e of the MMI waveguide 11 when the optical feedback elimination waveguide 15 is not formed. This is because an angle of radiation of the optical feedback scattered by the guided light reflection waveguide side surface 14 has a certain breadth, and if the intersection point 15e is set in this way, a structure is obtained in which the scattered light is effectively guided to the optical feedback elimination waveguide 15.

Similarly to FIG. 1A, in the optical waveguide element shown in FIG. 1B, fundamental propagation mode waveguides 13 are respectively connected to output tapered waveguides 13t. Then the optical feedback elimination waveguides 15 are provided on both sides of the input tapered waveguide 12t such that they sandwich the input tapered waveguide 12t. Sections corresponding to the guided light reflection waveguide side surface 14 and the optical feedback elimination waveguide 15 are indicated as a guided light reflection waveguide side surface 14' and an optical feedback elimination waveguide 15'. In this way, by the optical feedback elimination waveguides 15 being formed symmetrically with respect to the guiding direction, the optical feedback can be efficiently eliminated by the cladding layer. In particular, the optical waveguide element shown in FIG. 1B is optimal in cases of being used as a branching element in which light input to the input tapered waveguide 12t is branched into two outputs to the output tapered waveguides 13t.

The optical waveguide element shown in FIG. 1C is a 1 input 4 output optical waveguide element. Four output tapered waveguides 16t are provided and fundamental propagation mode waveguides 16 are connected to each of the output tapered waveguides 16t. When there are many of the output tapered waveguides 16t, in this manner, the amount of optical feedback that returns to the input tapered waveguide 12t also becomes greater, and it is particularly preferable to adopt the structure in which the optical feedback elimination waveguides 15 are provided on both sides of the input tapered waveguide 12t such that they sandwich the input tapered waveguide 12t.

The optical waveguide element shown in FIG. 1C is an element that is provided with the 4 output terminals (N=4) and thus an MMI waveguide 11" is a waveguide that can excite four types of propagation mode, namely, a zeroth-order to a third-order propagation mode.

The optical waveguide element according to the embodiment of the present invention is formed by forming the waveguide pattern structure comprised of the MMI waveguide 11, the input tapered waveguide 12t and the output tapered waveguides (13at and 13bt, 13t or 16t). Then, as shown in FIG. 1D, a waveguide core 3 that forms the waveguide pattern structure is enveloped by a cladding layer 2. When a distance between a bottom surface of the waveguide core 3 and a top surface of a silicon substrate 1 is set as 1 nm or more, it is possible to effectively suppress the light propagated through the waveguide core 3 from seeping into the silicon substrate 1.

<Optical Feedback Elimination Waveguide>

Modified examples of an optical feedback elimination waveguide will be explained with reference to FIG. 2A to 2E.

Figure 2A:
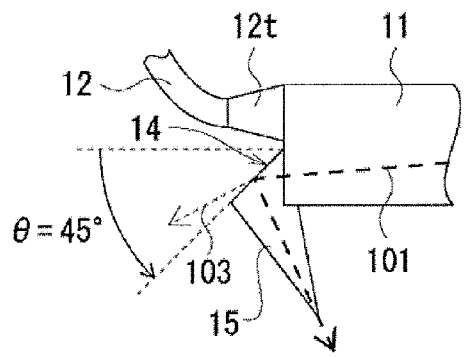
FIG. 2A is a basic schematic view contributing to an explanation of an optical feedback elimination waveguide that is provided with a guided light reflection waveguide side surface, and an explanation of a principle of operation thereof, in the waveguide pattern of a section of the optical feedback elimination waveguide.

The optical feedback elimination waveguide 15 shown in FIG. 2A is the optical feedback elimination waveguide 15 of the optical waveguide element shown in FIG. 1A, and a case is shown in which the angle θ formed between the guided light reflection waveguide side surface 14 and the guiding direction of the MMI waveguide 11 is 45 degrees. Even if full reflection conditions of the optical feedback are not satisfied by the guided light reflection waveguide side surface 14, the optical electric field component that passes through the guided light reflection waveguide side surface 14 and seeps into the cladding layer is not guided to the input tapered waveguide 12t. In other words, in this case, the optical feedback is not guided to the light reflection waveguide side surface 14 but becomes refracted light 103 and is eliminated into the cladding layer.

It is sufficient if the angle θ that determines the direction of the guided light reflection waveguide side surface 14 is set as a value that can be secured in a manufacturing process.

In order to reduce the amount of light reflected by the optical feedback elimination waveguide 15, it is sufficient to lessen the degree of taper. However, when this is done, it is necessary to lengthen the optical feedback elimination waveguide 15 and the size of the element becomes accordingly larger. The degree of the taper is determined while giving overall consideration to the amount of reflected light and the length of the waveguide.

Figure 2B:
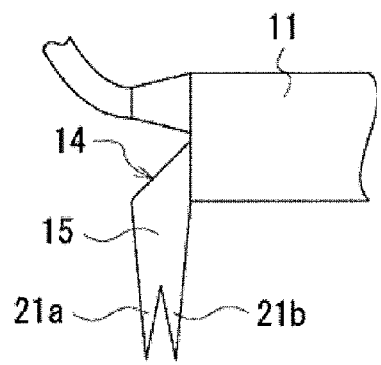
FIG. 2B is a configuration example in which splitter waveguides are provided, in the waveguide pattern of the section of the optical feedback elimination waveguide.

The optical feedback elimination waveguide 15 shown in FIG. 2B is characterized in that it is provided with a plurality of splitter waveguides 21a and 21b for splitting and guiding the reflected light reflected by the guided light reflection waveguide side surface 14. In this way, in comparison with the case in which only the single optical feedback elimination waveguide 15 is provided, it is possible to even more effectively eliminate the optical feedback to the cladding layer.

Figure 2C:
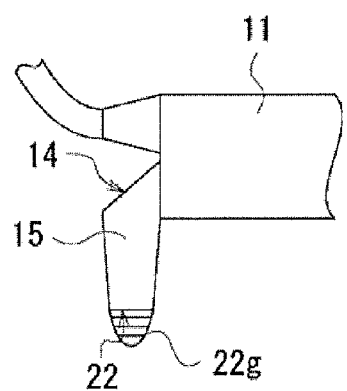
FIG. 2C is a configuration example in which a diffraction grating is provided, in the waveguide pattern of the section of the optical feedback elimination waveguide.

The optical feedback elimination waveguide 15 shown in FIG. 2C is characterized in that a diffraction grating 22g, which suppresses reflection of the reflected light, is provided on an output terminal 22 on a side opposite to the side of the optical feedback elimination waveguide 15 that is connected to the MMI waveguide 11. If a cycle of the diffraction grating 22g is set as a condition for the optical feedback to pass through or simultaneously as a condition for the optical feedback to be diffracted to the outside of the waveguide, the optical feedback component is effectively eliminated to the cladding layer.

Figure 2D:
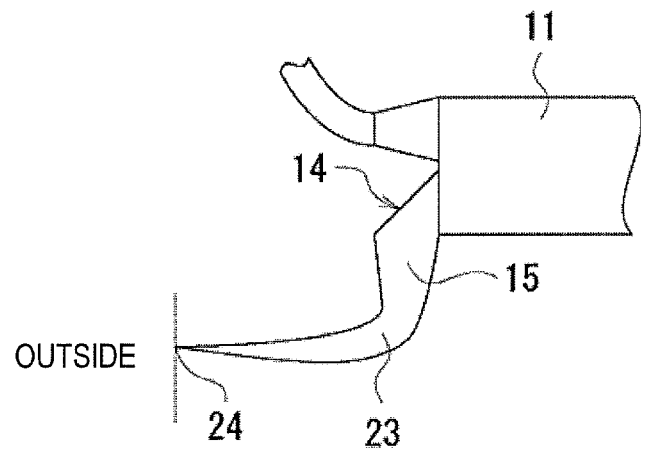
FIG. 2D shows a modified example of an optical feedback elimination waveguide, in the waveguide pattern of the section of the optical feedback elimination waveguide.

The optical feedback elimination waveguide 15 shown in FIG. 2D is characterized in that the optical feedback elimination waveguide 15 is formed such that it bends from a central portion 23, a leading end section 24 is oriented in a direction parallel to the guiding direction of the MMI waveguide 11 and the leading end section 24 reaches an end surface of the waveguide element such that the optical feedback is eliminated to the outside from the leading end portion 24. With this type of structure, as the optical feedback is eliminated to the outside, an optical feedback elimination effect is further enhanced in comparison to the elimination of the optical feedback to the cladding layer.

Figure 2E:
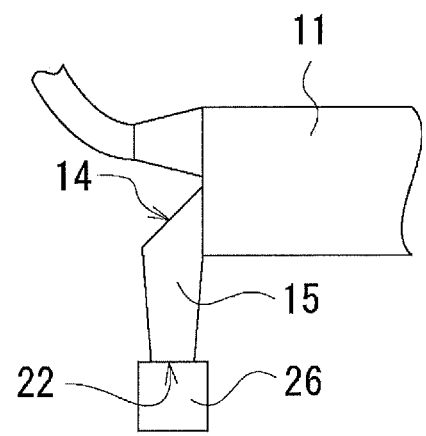
FIG. 2E shows a configuration example in which a light absorbing material is installed, in the waveguide pattern of the section of the optical feedback elimination waveguide.

The optical feedback elimination waveguide 15 shown in FIG. 2E is characterized in that a light absorption material 26, which suppresses reflection of the reflected light, is installed on the output terminal 22 on the opposite side to the side of the optical feedback elimination waveguide 15 that is connected to the MMI waveguide 11. The optical feedback component that is guided to the optical feedback elimination waveguide 15 is absorbed by the light absorption material 26 and thus an effect of eliminating the optical feedback is large. For example, Ge or the like can be used as the light absorption material 26.

<Numerical Simulation>

Figure 3:
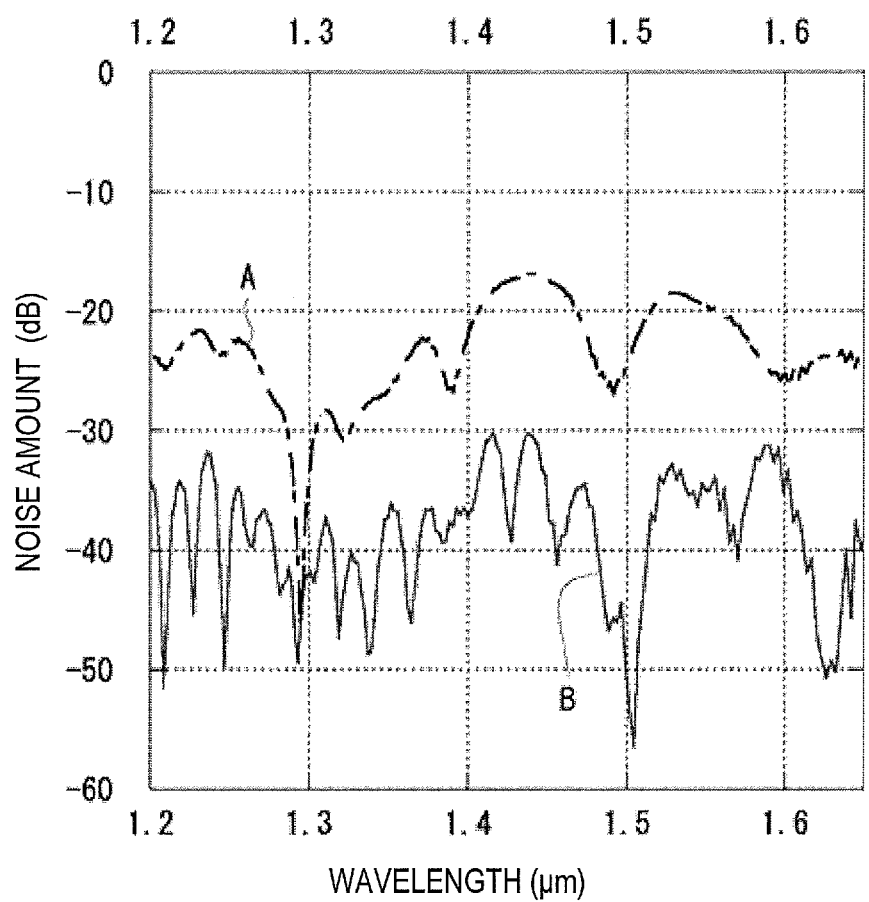
FIG. 3 is a diagram showing results of numerical simulation and a curve is shown for an amount of reflected light by a dotted line of a case in which the optical feedback elimination waveguide is not provided and a curve is shown for an amount of reflected light by a solid line of a case in which the optical feedback elimination waveguide is provided.

Results of a numerical simulation of effects of the optical feedback elimination waveguide 15 will be explained with reference to FIG. 3. A horizontal axis in FIG. 3 shows a wavelength using a scale of units in nm, and a vertical axis shows a scale in dB of a noise amount from light that is input from the waveguide 13a on the output terminal side of the MMI waveguide 11, and that is reflected and returns to the waveguide 13b on the output terminal side. In FIG. 3, a curve A that is shown by a single broken line shows a noise amount in a case in which the optical feedback elimination waveguide 15 is not provided, and a curve B that is shown by a solid line shows a noise amount in a case in which the optical feedback elimination waveguide 15 is provided.

The numerical simulation was performed on the optical waveguide element in the mode shown in FIG. 1A, using the finite-difference time-domain (FDTD) method. The conditions of the numerical simulation are described below.

A thickness of the silicon core was set as 300 nm, a width of the waveguide of the MMI waveguide 11 was set as 1610 nm, and a waveguide length was set as 49 nm. Further, a wide end of the input tapered waveguide 12t was set as 1040 nm and a narrow end of the input tapered waveguide 12t was set as 300 nm. A wide end of each of the output tapered waveguides 13at and 13bt was set as 680 nm and a narrow end of each of the output tapered waveguides 13at and 13bt was set as 300 nm. The waveguide length of both the input tapered waveguide 12t and the output tapered waveguides 13at and 13bt was set as 2 nm. The angle θ formed between the guided light reflection waveguide side surface 14 and the guiding direction of the MMI waveguide 11 was set as 45 degrees and a distance to a side surface facing the guided light reflection waveguide side surface 14 (a width of the waveguide) was set as 560 nm. The optical feedback elimination waveguide 15 has the tapered structure in which the waveguide width gradually changes from 700 nm to 100 nm toward the output terminal side and the waveguide length of the tapered structure section was set as 10 nm.

Further, the intersection point 15e between the guided light reflection waveguide side surface 14 and the side surface of the MMI waveguide 11 was set such that it is in a position that is 140 nm closer to the side of the MMI waveguide 11 than the input terminal 11e of the MMI waveguide 11 when the optical feedback elimination waveguide 15 is not formed.

As shown in FIG. 3, it can be seen that, in contrast to a noise amount of around −20 dB when the optical feedback elimination waveguide 15 is not provided, as shown by the curve A, the noise amount is −30 dB or lower when the optical feedback elimination waveguide 15 is provided, as shown by the curve B. It can be said that the noise amount is reduced by approximately 10 dB by adopting the structure in which the optical feedback elimination waveguide 15 is provided.

<Optical Waveguide Element Manufacturing Method>

The optical waveguide element according to the embodiment of the present invention that is formed by the waveguide pattern structure comprised of the MMI waveguide 11, the input tapered waveguide 12*t* and the output tapered waveguides (13*at* and 13*bt*, 13*t*, or 16*t*) can be formed, for example, by obtaining an SOI substrate and performing the following processes. The SOI substrate is widely obtainable as a commercial product and a silicon oxide layer is formed on a silicon substrate, and a silicon layer having a thickness equal to a thickness dimension of a waveguide is formed on top of the silicon oxide layer.

Dry etching is performed on the silicon layer formed on top of the silicon oxide layer of the SOI substrate, such that the above-described waveguide pattern structure remains and the silicon layer is removed from portions other than the waveguide pattern. After the dry etching process, the waveguide pattern that remains after the etching process forms the core of the waveguide structure and a silicon oxide layer that is a cladding layer enveloping the core is formed as an upper portion cladding layer by chemical vapor deposition (CVD) or the like. Then, polishing is performed such that the upper surface of the silicon oxide layer is flat, and the silicon oxide layer is thus formed as the upper portion cladding layer.

The silicon oxide layer that is the cladding layer is configured such that a lower portion cladding layer is formed by a silicon oxide layer that has already been formed on the silicon substrate when the SOI substrate is obtained, and the upper portion cladding layer is formed by the silicon oxide layer by CVD after the core has been formed. The silicon oxide layer that forms the cladding layer is thus formed. In FIG. 1D, the upper portion cladding layer and the lower portion cladding layer are not distinguished and are shown together as the cladding layer 2.

When the light absorption material 26 that suppresses the reflection of the light reflected on the output terminal 22 is provided, as in the optical feedback elimination waveguide 15 shown in FIG. 2E, after the dry etching has been performed and the above-described waveguide pattern structure remains, next, a process may be performed to mount the light absorption material 26 on a portion close to the output terminal 22 of the optical feedback elimination waveguide 15. In this case, the silicon waveguide core is present beneath the light absorption material 26, and as the light component that leaks outside the core is absorbed by the light absorption material 26, the light that is propagated through this silicon waveguide core is effectively absorbed by the light absorption material 26.

In this way, as it is possible to form the optical waveguide element according to the embodiment of the present invention using the SOI substrate and by a known etching process and CVD etc., the optical waveguide element can be easily formed at low cost with excellent mass-productivity.

Heretofore, preferred embodiments of the present invention have been described in detail with reference to the appended drawings, but the present invention is not limited thereto. It should be understood by those skilled in the art that various changes and alterations may be made without departing from the spirit and scope of the appended claims.

What is claimed is:

1. An optical waveguide element including a waveguide core formed of silicon, and a cladding layer formed of a material identical to the waveguide core for enveloping the waveguide core, the optical waveguide element comprising:

a high-order propagation mode waveguide;

a single input tapered waveguide that is provided on an input terminal of the high-order propagation mode waveguide;

a plurality of output tapered waveguides that are provided on an output terminal of the high-order propagation mode waveguide; and an optical feedback elimination waveguide that is provided on the input terminal and disposed alongside the input tapered waveguide;

wherein the input tapered waveguide and the output tapered waveguides are tapered waveguides in which a waveguide width becomes gradually narrower the greater the separation from a terminal of connection to the high-order propagation mode waveguide, and the optical feedback elimination waveguide eliminates reflected light into the cladding layer, the reflected light being input from the input terminal and reflected by the output terminal.

2. The optical waveguide element according to claim 1, wherein a number N of the output tapered waveguides is provided, where N is an integer of 2 or more, and a waveguide width of the high-order propagation mode waveguide is set to be capable of propagating at least N types of a propagation mode.

3. The optical waveguide element according to claim 1, wherein the optical feedback elimination waveguides are provided on both sides of and sandwich the input tapered waveguide.

4. The optical waveguide element according to claim 1, wherein a fundamental propagation mode waveguide is provided on the input tapered waveguide and the output tapered waveguides.

5. The optical waveguide element according to claim 1, wherein the optical feedback elimination waveguide has a guided light reflection waveguide side surface that reflects guided light, which is guided to the optical feedback elimination waveguide, in a direction that is displaced from a direction directly opposite to a guiding direction of the high-order propagation mode waveguide.

6. The optical waveguide element according to claim 5, wherein the optical feedback elimination waveguide includes a plurality of splitter waveguides that split and eliminate the reflected light reflected by the guided light reflection waveguide side surface.

7. The optical waveguide element according to claim 1, wherein the optical feedback elimination waveguide is a tapered waveguide in which a waveguide width becomes gradually narrower toward a leading end of the optical feedback elimination waveguide from a terminal of connection to the high-order propagation mode waveguide.

8. The optical waveguide element according to claim 1, wherein a leading end of the optical feedback elimination waveguide reaches an end surface of the optical waveguide element.

9. The optical waveguide element according to claim 1, wherein the optical feedback elimination waveguide includes a diffraction grating, on an output terminal that is on a side opposite to a side on which the optical feedback elimination waveguide is connected to the high-order propagation mode waveguide.

10. The optical waveguide element according to claim 1, wherein
the optical feedback elimination waveguide includes a light absorption material on an output terminal that is on the side opposite to the side on which the optical feedback elimination waveguide is connected to the high-order propagation mode waveguide.

* * * * *